(12) United States Patent
Koehler et al.

(10) Patent No.: US 10,835,193 B2
(45) Date of Patent: Nov. 17, 2020

(54) SOURCE GRATING FOR X-RAY IMAGING

(71) Applicant: KONINKLIJKE PHILIPS N.V., Eindhoven (NL)

(72) Inventors: Thomas Koehler, Norderstedt (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/329,807

(22) PCT Filed: Aug. 30, 2017

(86) PCT No.: PCT/EP2017/071806
§ 371 (c)(1),
(2) Date: Mar. 1, 2019

(87) PCT Pub. No.: WO2018/046377
PCT Pub. Date: Mar. 15, 2018

(65) Prior Publication Data
US 2019/0216416 A1    Jul. 18, 2019

(30) Foreign Application Priority Data

Sep. 8, 2016  (EP) .................................. 16187753

(51) Int. Cl.
*A61B 6/03*        (2006.01)
*G02B 5/18*        (2006.01)
(Continued)

(52) U.S. Cl.
CPC ............ *A61B 6/4291* (2013.01); *A61B 6/484* (2013.01); *G02B 5/1838* (2013.01);
(Continued)

(58) Field of Classification Search
CPC ..... A61B 6/4092; A61B 6/4291; A61B 6/484; G01N 23/041; G02B 5/1838;
(Continued)

(56) References Cited

U.S. PATENT DOCUMENTS

| 2012/0020454 | A1 | 1/2012 | Murakoshi |
| 2013/0032734 | A1* | 2/2013 | Santori ............. G01N 21/6456 250/458.1 |
| 2013/0164457 | A1 | 6/2013 | Ehlers |
| 2014/0314374 | A1* | 10/2014 | Fattal .................... G02B 6/124 385/33 |

(Continued)

FOREIGN PATENT DOCUMENTS

| WO | 2008027412 | 3/2008 |
| WO | 2012/104770 | 8/2012 |

(Continued)

OTHER PUBLICATIONS

Yaroshenko, et al.: "Non-binary phase gratings for x-ray imaging with a compact Talbot interferometer", Optics Express, vol. 22, No. 1 (2014), pp. 548-556.
Kohler et al in "Iterative reconstruction for differential phase contrast imaging using spherically symmetric basis functions", Med Phys 38(8) (2011).

(Continued)

*Primary Examiner* — Mark R Gaworecki
(74) *Attorney, Agent, or Firm* — Larry Liberchuk

(57) ABSTRACT

A source grating structure (G0) for interferometric X-ray imaging cable of generating a non-uniform intensity profile behind a surface (S) of the grating structure when exposed to X-ray radiation.

6 Claims, 5 Drawing Sheets

(51) Int. Cl.
  *G21K 1/02* (2006.01)
  *G21K 1/06* (2006.01)
  *G21K 1/10* (2006.01)
  *A61B 6/00* (2006.01)
  *G01N 23/041* (2018.01)

(52) U.S. Cl.
  CPC ........... G02B 5/1871 (2013.01); G21K 1/025 (2013.01); G21K 1/06 (2013.01); G21K 1/10 (2013.01); *A61B 6/4092* (2013.01); *G01N 23/041* (2018.02); *G21K 2207/005* (2013.01)

(58) Field of Classification Search
  CPC ........ G02B 5/1871; G21K 1/025; G21K 1/06; G21K 1/10; G21K 2207/005
  See application file for complete search history.

(56) References Cited

U.S. PATENT DOCUMENTS

2015/0279497 A1    10/2015    Den
2015/0362641 A1    12/2015    Boyraz

FOREIGN PATENT DOCUMENTS

WO    2012/107862    8/2012
WO    2013/171657    11/2013

OTHER PUBLICATIONS

Pfeiffer et al., "Phase retrieval and differential phase-contrast imaging with low-brilliance X-ray sources", Nature Physics, 2006.

* cited by examiner

SOURCE GRATING FOR X-RAY IMAGING

CROSS REFERENCE TO RELATED APPLICATIONS

This application is the U.S. National Phase application under 35 U.S.C. § 371 of International Application No. PCT/EP2017/071806 filed Aug. 30, 2017 published as WO 2018/046377 on Mar. 15, 2018, which claims the benefit of European Patent Application Number 16187753.5 filed Sep. 8, 2016. These applications are hereby incorporated by reference herein.

FIELD OF THE INVENTION

The invention relates to a grating structure and an imaging system.

BACKGROUND OF THE INVENTION

Grating-based phase-contrast and dark-field imaging is a promising technology to enhance the diagnostic quality of x-ray equipment CT (computed tomography). In CT (but not only there), an X-ray beam intensity is usually modulated along the fan-angle of the system by means of a bow-tie filter. This filter aims at ensuring a higher flux for the central rays which will be typically attenuated the most by the imaged object, eg a patient.

SUMMARY OF THE INVENTION

There may therefore be a need for alternative gratings and/or imagers. The object of the present invention is solved by the subject matter of the independent claims where further embodiments are incorporated in the dependent claims. It should be noted that the following described aspect of the invention equally applies to the imaging system.

According to a first aspect of the invention there is provided a source grating structure for interferometric X-ray imaging cable of generating a non-uniform intensity profile behind a surface of the grating structure when exposed to X-ray radiation.

According to one embodiment, said intensity profile has at least one local maximum away from an edge of said surface.

According to one embodiment, the grating structure comprises a set of absorbing elements arranged in a periodic pattern to form said surface, said set including at least two absorbing elements, one proximal and one distal to said edge, wherein a material density of the proximal absorbing element is higher than the material density of the distal proximal element.

According to one embodiment, the grating structure comprises a set of absorbing elements arranged in a periodic pattern to form said surface, said set including at least two absorbing elements, one proximal and one distal to said edge, the at least one proximal absorbing element having a greater depth perpendicular to said surface than the depth of the distal proximal element.

According to one embodiment, the grating structure has a non-uniform duty cycle profile.

According to one embodiment, the duty cycle profile has at least one local maximum away from the edge of said surface.

According to one embodiment, the grating structure is configured to compensate, in a at least one direction, a Heel effect. Because of the Heel effect, parts of an X-ray beam generated at an X-ray source have different intensities. The grating compensates for this by allowing those parts of the X-ray beam to pass with less intensity loss that have experienced a higher intensity loss due to the Heel effect and vice versa.

More particularly and according to one embodiment, the grating structure is configured so that the intensity profile decreases in a direction along a rotational axis of an X-ray imaging system.

According to one aspect there is provided an imaging system comprising:
 an X-ray source;
 an X-ray sensitive detector;
 an examination region between the X-ray source and the X-ray sensitive detector for receiving an object to be imaged;
 a grating structure of any one of previously mentioned embodiments arranged between the X-ray source and the object when said object resides in said imaging region. According to one embodiment, said imaging system is a rotational one, in particular, a computed tomography imaging system.

In other words, what is proposed herein is to use a source grating, not only to improve coherence but in addition to compensate or otherwise account for a range of other physical or technical effects that have a bearing on X-ray imaging. For instance, in one embodiment it is proposed to integrate a bow-tie filter functionality into the source grating for interferometric imaging. The need for a bow-tie filter is thus obsolete. This allows securing several advantages: scatter radiation can be reduced compared to a design with separate conventional bow-tie filter. Improved visibility for large fan-angles can be secured, and the proposed combination solution frees up space in the imaging system.

Specifically and according to one of the embodiment mentioned above, the duty cycle decreases from a center portion of the grating towards larger ray angles. The decreased duty cycle leads to a reduction of the x-ray flux. Use of a separate bow-tie filter is hence no longer required. As a positive side effect, the spatial coherence of the outer rays is improved, which will lead to a better overall image quality. Similar advantages can be secured by varying the depth of the absorber elements and/or the density of absorber element material as mentioned above.

In another embodiment, the grating structure is configured to compensate instead or on addition for the Heel effect in an X-ray source of the X-ray imaging system.

The grating may in addition or instead be configured to account, via its generated intensity profile, for other physical/technical effects, either singly or in combination.

The grating structure is either planar or curved, the latter option being preferable when the imager is rotational, such as CT or C-arm. Specifically, the source grating is at least partly curved for focus on a location of a focal spot of the X-ray source. Specifically, the curvature of the source grating determines the distance at which said grating is to be placed from the focal spot so the non-uniform illumination profile can best be observed when the grating is held into the X-ray beam.

The source grating is capable of producing the non-uniform intensity profile on its own, that is, without intervening objects (in particular other grating(s)), when the source grating is placed in the X-ray beam of an X-ray source.

BRIEF DESCRIPTION OF THE DRAWINGS

Exemplary embodiments of the invention will now be described with reference to the following drawings (which are not necessarily to scale) wherein.

DETAILED DESCRIPTION OF EMBODIMENTS

Figure 1:
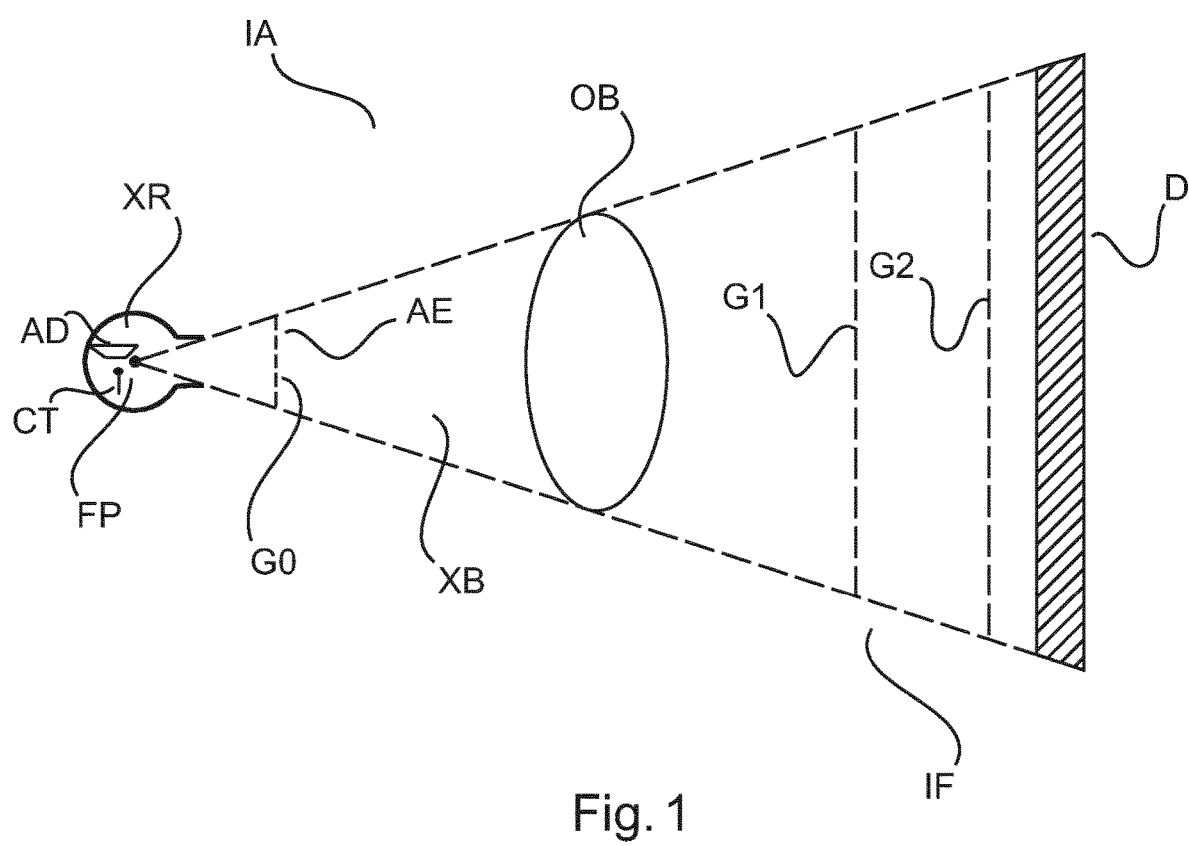
FIG. 1 shows in a schematic fashion portions of an interferometric x-ray imaging system.

With reference to FIG. 1, there is shown a schematic block diagram of an X-ray imaging apparatus ("imager") IA including an interferometric arrangement IF.

The interferometric arrangement IF includes two or three gratings arranged between an X-ray source XR and a detector D. There is an examination region between the X-ray source and the detector and between at least two of the gratings. The imaging or examination region is suitable to receive an object OB to be imaged. The object is animate or inanimate. An animate object includes for instance an animal or human patient or at least a part thereof (region of interest) to be imaged.

X-ray radiation beam XB emitted from a focal spot FS of X-ray source XR interacts with the gratings of the interferometer IF and the object OB and is then incident on the radiation sensitive surface of detector D formed by a plurality of detector pixels. The incident radiation causes electrical signals which are picked up by a data acquisition system DAS and are converted into digital projection data. Because of interaction with the interferometer IF (more of which further below), this projection data is referred to herein as interferometric projection data. The X-ray source XR comprises an anode AD and a cathode CT arranged in a vacuum tube. A voltage is applied across anode and cathode. This causes an electron beam. The electron beam impacts the anode at the focal spot FS. The electron beam interacts with the anode material and this produces the X-ray beam. In general, but not necessarily in all embodiments, the X-ray beam XB exits the tube at a direction perpendicular to an axis between the anode and the cathode.

The interferometric projection data can be reconstructed into cross-section imagery of the object, on which more further below.

Preferably, the imager IX is arranged as a tomographic imaging apparatus the optical axis which is shown in a horizontal arrangement running from the focal point of the X-ray source to the detector. This axis can be changed so as to acquire projection data from multiple projection directions around the object (not necessarily in a full revolution, a 180° rotation may be sufficient, or even less in tomosynthesis, etc). In particular the X-ray source and/or the detector with the interferometer is rotatable in a rotation plane (having a rotation axis Z) around the object OB. The object OB is thought to reside at an iso-center in the examination region whilst at least the X-ray source (in some embodiments together with the detector) and some or all of the interferometer rotates around the object in a projection data acquisition operation. In yet other embodiments, the relative rotation is achieved by rotation of the object OB.) By optionally advancing the object through the examination region, multiple cross sectional images can be obtained which can be combined together to form a 3D image volume of the object.

The imager IX is capable of producing phase contrast and/or dark field (cross section) images. In some embodiments, but not necessarily in all embodiments, there is also a third image channel for a conventional attenuation (cross section) image. The attenuation image represents spatial distribution of attenuation coefficient across the object in the respective section plane, whilst the phase contrast and the dark-field images represent spatial distribution of refractive activity of the object and small angle scattering (caused by micro structures in the object), respectively. Each of these images may have diagnostic value for a given diagnostic task at hand.

The capability of imaging for phase contrast and/or dark field signals comes about by operation of the interferometer IF. The interferometer IF comprises in one embodiment two gratings G1 (sometimes referred to a phase grating) and G2 (sometimes referred to as analyzer grating) arranged at a specific distance to each other. Preferably G2 is an absorber grating and G1 is a phase or absorber grating. In one embodiment, the two gratings are arranged downstream the examination region (in particular the objet OB), so that, during the imaging, the two gratings are situated between the object and the detector. The examination region in this arrangement is then between X-ray source and the grating pack formed by the two gratings G1 and G2.

There is a source grating G0 (on which more below) arranged between focal spot FS of XR source and the object to increase the coherence of the emitted radiation. The described interferometric set up is known as Talbot (without G0 grating) or Talbot-Lau (with G0 grating) interferometer. The distance between G0 and G1 and between G1 and G2 are specifically adjusted according to the Talbot-Lau set up that has been described elsewhere. The distances between G0 and G1 and between G1 and G2 must be finely tuned to fit the requirements of Talbot distance which in turn is a function of the "pitch" (that is, the spatial period of the grating rulings) of the respective grating. However, if G1 is configured as an absorber grating, there is more freedom to change distances and pitches. The same holds true if G1 is a phase grating, but with a non-rectangular cross section (non-binary grating). See for instance, A Yaroshenko et al in "Non-binary phase gratings for x-ray imaging with a compact Talbot interferometer", Optics Express, Vol 22, No 1 (2014), pp 548-556.

As an alternative to the above described interferometer, inverse grating geometries are also envisaged herein where one of the two interferometer gratings (G1) is positioned between the XR source and the object OB in the examination region whereas the other (G2) is between the examination region and the detector.

Irrespective of the grating geometry used, assuming for a moment that there is no object OB present in the examination region the coherent radiation emerges on the far side of G0, interacts with the interferometer G1, G2 to produce an interference fringe pattern, in particular, fringes of a Moiré pattern, which can be detected at the detector D. To achieve this pattern, the two gratings of the interferometer are slightly de-tuned (for instance by slightly tilting the two gratings G1, G2 relative to each other). This Moiré pattern, which we will refer to herein the "reference fringe pattern", has a certain fixed reference phase, reference visibility and intensity, all of which are encoded by the reference fringe pattern. The reference pattern is solely the result of the interferometer's presence (for a given radiation density). In that sense it can be said these quantities, in particular the reference phase, is a property of the interferometer as such and it is therefore apt to say that the interferometer "has" said reference phase, said reference intensity and said reference visibility.

Now, if the object OB to be imaged is introduced into the examination region this object will interact with the coherent radiation to which it is now exposed to, in other words, the coherent radiation will be partly absorbed, refracted and scattered. The result of this object interaction is yet another fringe pattern, different from the reference pattern, which will be observed at detector D. The interference pattern induced by the presence of object OB can be understood as a perturbed version of the reference fringe pattern when there was no object present in the examination region. The reference data of the reference fringe pattern fp are usually acquired in calibration measurement also referred to as an "air scan". The actual object measurements are then acquired in a second scan when the object to be imaged is present in the examination region. The perturbed reference fringe pattern can be processed by known reconstruction algorithm such as described Kohler et al in "Iterative reconstruction for differential phase contrast imaging using spherically symmetric basis functions", Med Phys 38(8) (2011) or Applicant's "Dark-field computed tomography" as described in WO 2013/171657 to obtain the desired phase contrast and/or dark-field imagery.

Turing now in more detail to the interferometric grating equipment, in addition to the interferometric gratings G1, and, if applicable, grating G2, of the interferometer IF, there arranged the additional grating structure G0, referred to herein as "source grating". The source grating G0 is mounted close to the x-ray source, for instance is integrated in an X-ray tube housing at the egress window of the x-ray source XR but at any rate this source grating structure G0 is arranged between the x-ray source and the remaining gratings, in particular G1.

The source gating G0 modifies the X-ray radiation that passes through it. The source grating G0 as envisaged herein serves a dual purpose. For one, grating G0 acts to increases coherence of the x-ray radiation that passed through the grating, relative to the X-radiation as emitted by the source XR.

Figure 2:
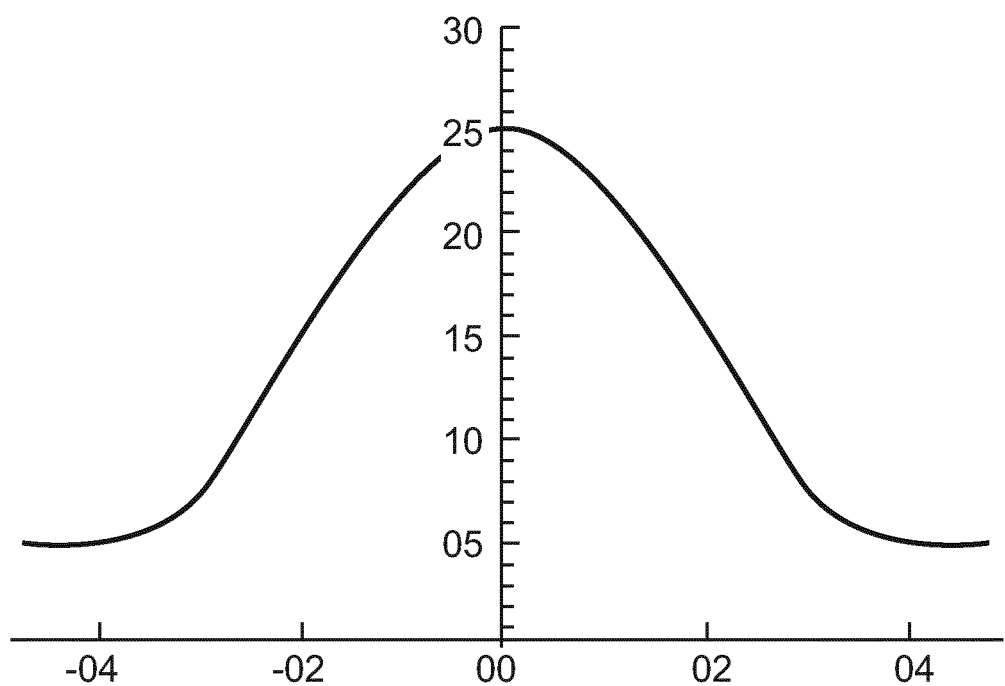
FIG. 2 shows an intensity profile achievable with an interferometric grating structure according to one embodiment.

In addition to this coherency increasing functionality, grating structure G0 is further configured to modulate the intensity or transmission profile of the x-ray radiation that emerges downstream the grating G0 so as to conform to a shape of the object to be imaged OB or to a shape prototype of the object. More particularly, the grating structure G0 operates similar to a bowtie filter used in existing CT x-ray scanners. In other words it is configured to ensure that the intensity of the radiation beam is reduced at portions of the beam where the expected path length through the object is short and to allow for a larger intensity where the expected path length is large. It has been found that an elliptic shape well represents the general overall path length characteristics of a human patient taken in cross section perpendicular to the patient's longitudinal axis. The intensity is then modulated inversely to a mean path length through the elliptic shape prototype (it is apt to speak of a "mean" path length as the path length through an elliptic shape changes during rotation). The intensity prolife caused by the grating G0 has a local maximum or peak at about a central portion of an imaginary elliptic cross section of the subject OB, whilst the intensity profile decreases either side of said peak as shown in FIG. 2. FIG. 2 illustrates an equivalent manner of describing the intensity profile shape as envisaged herein and generated by grating G0 for X-radiation passing through said grating G0. Intensity (vertical axis) downstream or "behind" said grating is graphed versus angular divergence a of rays of the beam XB from an optical axis (0°) of the imager IS. For instance, the angular divergence may correspond to a fan angle of the beam, but this is not limiting as the present disclosure is not limited to beam type such as fan beam. Beams of any divergent geometry such as cone beam are also envisaged herein. Even parallel beams are envisaged, in which case the divergence angle is replaced by perpendicular distance from the optical axis. It will be understood that the intensity profile may be measured along an arbitrary line behind the grating surface S. Also, the bell shaped profile of FIG. 2 should be understood purely qualitatively and admits a multitude of variations, all envisaged herein. In particular, although a profile having (as in FIG. 2) a single local maximum is envisaged as the preferred embodiment, this does not preclude other embodiments with intensity profiles having multiple maxima, depending on the cross-section profile of the object one wishes to image. For instance, in the non-medical field such as non-destructive material testing, if one wishes to image dumbbell shaped objects, a profile with multiple maxima may be called for.

Figure 3:
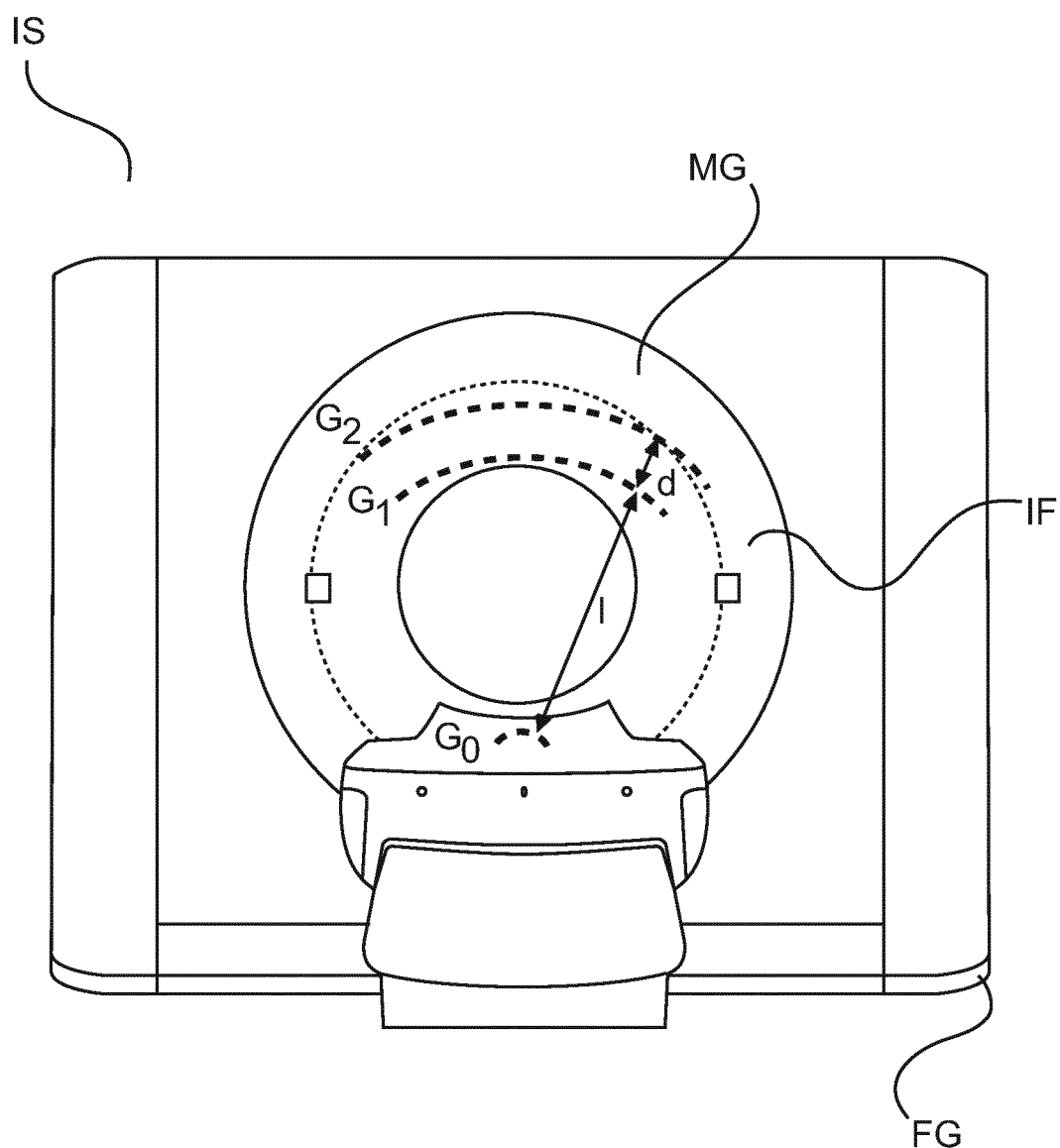
FIG. 3 shows an interferometric x-ray imaging system according to one embodiment.

It will be understood that the proposed setup is of particular application of rotational X-ray imagers such as CT or C-arm so the optical axis is rotatable but this is not to exclude more traditional X-ray radiography system with a fixed optical axis. In relation to rotational imagers IS, reference is made to FIG. 3 which shows in frontal view a CT scanner embodiment of the interferometric imaging system IS mainly envisaged herein. The rotation axis Z extends into the drawing plane in of FIG. 3. The scanner IS in FIG. 3 is of the $3^{rd}$ generation. In these types of scanners, the x-ray source XR and the detector D are arranged opposite each other across the examination region. X-ray source XR and detector DR are arranged in a moveable gantry MG that is moveably arranged in a fixed gantry FG to allow rotation of the x-ray source together with the detector around the examination region and hence around the patient. The examination region corresponds to the hole through the gantry FG, thus conferring to the imager IS the familiar "doughnut shape". It is for note however that FIG. 3 is merely an exemplary embodiment as scanners of the $1^{st}$, $2^{nd}$ and $4^{th}$ generation are not excluded herein in alternative embodiments.

FIG. 3 further shows the interferometer IF integrated into the CT scanner IS. The two gratings G1 and G2 are arranged at the required Talbot distance D before the detector D (not shown) whilst the additional grating structure G0 is arranged at the x-ray source. The grating structure of the interferometer and/or the addition grating structure G0 may be planar as in FIG. 1 but are preferably curved as in FIG. 3 to form partial surfaces of imaginary concentric cylinders centered about the focal spot of the X-ray source XR.

Turning now in more detail to grating G0, this is arranged as an absorber grating, similar to the analyzer grating G2 (if any) of the interferometer IF. In other words, grating G0 includes a plurality of in general elongate absorber elements AE or "bars" that are laid out and in a periodic pattern to form a surface S (planar or curved) where the incoming radiation emitted from x-ray source XR is received. The absorber elements are preferably formed from relatively high Z element such as lead, tungsten, gold or other to achieve good (that is, substantially complete) local absorption of the X-radiation.

Dual to the periodicity of system of absorber bars AE there is a complimentary pattern of non-absorbing inter-spaces defined between any two, neighboring absorber bars AE. The inter-space-and-bars system allows increasing the spatial coherence of the x-ray radiation that emerges from the grating G0 after passage of the incoming radiation through the grating G0. The grating G0 radiation blocking bars and the inter-spaces act as a collimator that divides the beam into a plurality of virtual source lines that radiate together more coherently. In addition to coherency enhancement, and as mentioned above, the bar elements AE are configured to achieve, in particular, the intensity profile as per FIG. 2. Said differently and structurally, the intensities that can be measured behind the grating G0 are becoming smaller towards edge portions E1, E2. The intensity increases with distance away from the edge or edges E1,E2 of the grating surface S and, preferably, peaks at a center portion of the surface S of the grating.

Figure 4:
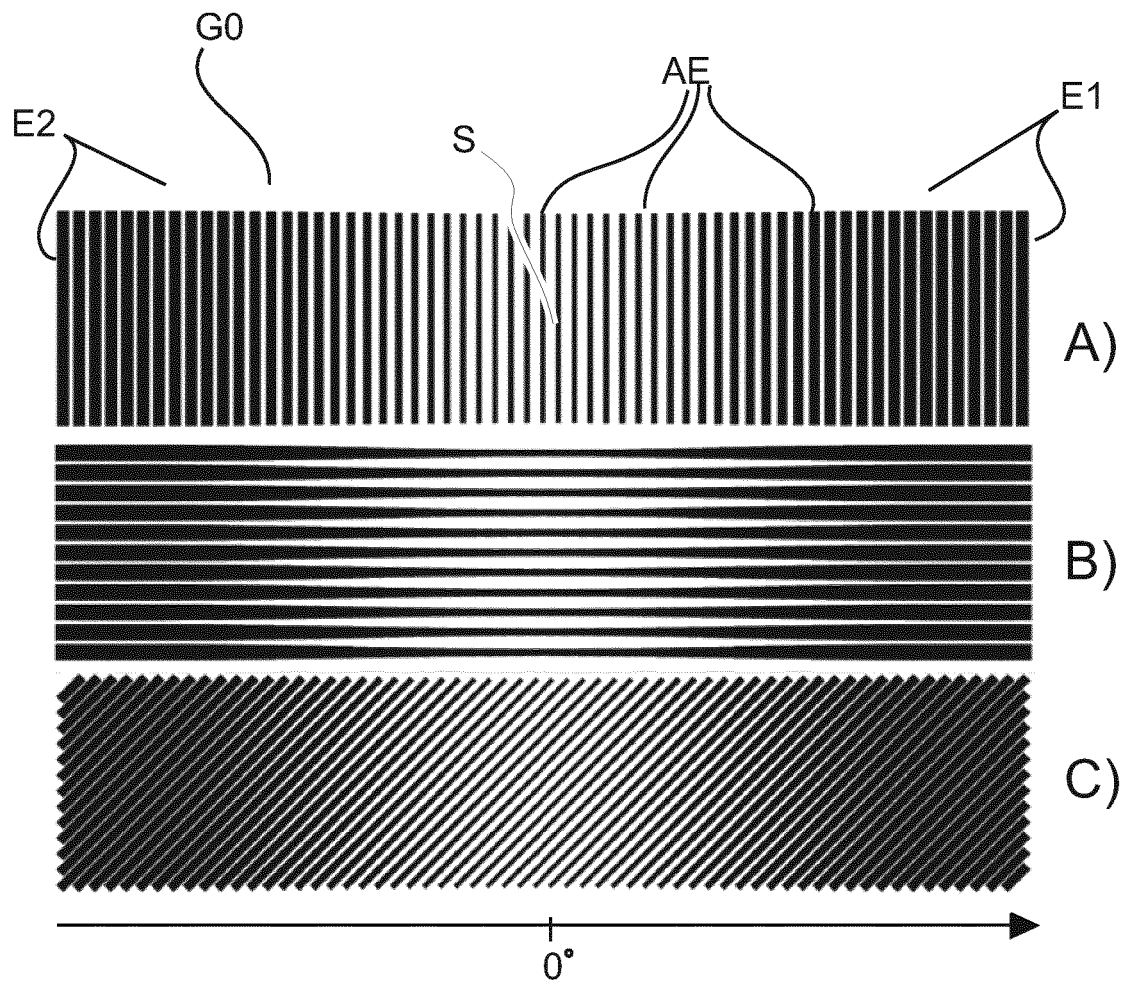
FIG. 4 shows different embodiments of grating structures in plan view.

An example of how the grating structure is configured to achieve this intensity profile is shown in FIG. 4A)-C). FIG. 4 shows three embodiments of grating structure G0 envisaged herein. FIG. 4A)-C) affords respective plan views on grating G0 as seen from the x-ray source XR.

In embodiments A), the desired intensity profile is achieved by corresponding modulation of a duty cycle of the grating structure G0. The duty cycle is a local property of the grating and can be expressed as the ratio between the width (that is, the spatial extent parallel to the surface) of a grating absorbing element AE versus the width (spatial extent parallel to the surface) of its neighboring inter-space. The duty cycle is usually expressed as a number, and the smaller the number is, the wider the absorber elements relative to the width of the inter-space. The duty cycle in FIG. 4A varies with distance α (eg, fan angle) from the center portion surface S and hence with distance from the optical axis. In particular, the duty cycle decreases from the center portion towards the edge portions E1 and E2. A monotonic decrease of the duty cycle form the center towards edges E1, E2 is preferable but alternative embodiments are also envisaged where the duty cycle does not decrease monotonically but rather remains constant sectionwise along the surface. For a given grating, a duty cycle profile may be defined as a curve formed from local duty cycles measured locally at sample points on the grating along an arbitrary line (eg, center line) that extends on the surface S, not necessarily perpendicular to the direction in which the bars run. This duty cycle profile has then a local maximum located away from the edges E1, E2, preferably at a center portion of the gating surface.

In embodiment as per FIG. 4A) the duty cycle variation is achieved by having the bar elements increase in thickness measured in a direction perpendicular to the optical axis or parallel to the surface. Whilst the thickness of each absorber element AE in FIG. 4A) is constant for any given absorber element AE, this thickness decreases for absorber elements AE away from the center of the surface of the grating. In other words, the further away from the center, the thicker the bars are. As further illustrated in FIG. 4A), in addition to the thickness of the absorber elements increasing with the distance from the surface S center portion, reciprocal thereto, a thickness of the inter-space distance decreases.

In an alternative embodiment and as shown in FIG. 4B), it is the thickness of the absorber elements (perpendicular to the optical axis) that changes with distance from the center of grating surface S. In particular, for any given absorber element its thickness towards the center portion of the surface S is smaller as compared to its thickness at the edge portions E1, E2 of the grating. In other words, the absorber elements have constriction in the central region of the surface S. Said differently, in FIG. 4A, the duty cycle varies across the course of the absorber elements whilst in FIG. 4B the duty cycle varies along the course of the absorber elements.

The embodiment in FIG. 4C) is similar to that in Figure B but there the course of the absorber element is slanted relative to the rotation plane of the x-ray source of the imager IS. In distinction to this, in FIGS. 4A), B), the absorber elements AE run either parallel (as in FIG. 4A)) or perpendicular to (as in 4B)) to the rotation plane. In FIG. 4C), the bars AE are oriented at about 45° relative to the plane of source XR rotation. However, any other angular inclination relative to the rotation plane is also envisaged. In particular, variants of FIG. 4A,B) are also envisaged where the absorber elements run at an angle other than parallel or perpendicular to the rotation plane.

In one embodiment (not shown), the depth or height of the absorbers elements is modulated to achieve the desired bell curve shaped intensity profile. The depth of the absorber element is its respective extension in propagation direction of the x-radiation, or, said differently, its extension along the optical axis, is perpendicular to surface S. In plan view of FIG. 4, the depth extends into the drawing plane. In particular, in this embodiment where the bell shaped intensity profile is achieved by depth modulation, absorber elements situated towards (or proximal to) the edges E1, E2 of the surface S have a greater depth than those away (distal) from the edge towards at the center portion of S. Again, a monotonic increase of depth is preferable but this is not necessarily so in other embodiments where the depth of the absorber elements does not necessarily increase in a monotonic fashion from the center towards the edge portions.

As yet a further embodiment, the absorber elements may be formed from different materials rather than being formed from the same material as envisaged in the embodiments so far discussed. For instance, in this embodiment one may form absorber elements at the edge from a material of higher density (high Z elements) than the material used for those absorber elements located at or towards the center of Surface S. In other words, the qualitative intensity profile as per FIG. 2 is achieved by absorber material type or density modulation.

The embodiments with depth or material type/density modulation may be combined with any of the FIG. 4 embodiments. That is, although the absorber element depth in the FIG. 4 embodiments and their variants are envisaged as constant, this may not be necessarily so as the depth modulation may be combined with any of the embodiments of FIG. 4 or any of their variants. In addition or instead, the absorber elements AE may be formed as explained from different materials (with different density). It will be understood that if the intensity profile has multiple maxima (as mentioned above), the duty cycle profile, depth profile etc will likewise have multiple extrema.

In sum, the decreased duty cycle (as a function of ray angle α and hence distance from the grating surface S center) or the depth or material density modulation leads to a reduction of the x-ray flux. This makes in particular the use of a separate bow-tie filter obsolete. As a positive side effect, the spatial coherence of the outer rays is improved, which will lead to a better overall image quality.

The dual purpose grating structure G0 envisaged for intensity modulation and beam coherence enhancement may be manufactured by in a manifold ways, all envisaged herein. For instance, in one embodiment the grating structure G0 is cut as a mask or stencil by laser cutting or other techniques from a single high Z material sheet such as a tungsten sheet or other.

In other embodiments the grating structure is assembled from different parts rather than being formed monolithically. For instance, in one embodiment trenches are formed by etching or laser cutting or otherwise into a carrier substrate such as silicon or other. The trenches are set apart at the required distance to form the inter-space elements. These trenches are then filled with an alloy or a high Z material such as gold, tungsten, lead or other to manufacture the grating G0. The width and/or depth of the trenches and hence that of the absorber elements can be varied by using for instance a laser beam of a different width or by running a laser beam of constant width multiple times (with relative off-set) across the substrate material to cut the trenches with variable thickness to achieve the desired modulation.

Although in the above embodiments the grating structure G0 has been assumed as planar this is not to restrict other embodiments that are curved as indicated in FIG. 3. All of the above discussed grating embodiments in FIG. 4 and thereafter can be combined with curved gratings. The curvature of the grating G0 (and that of G1 and G2) allows focusing the gratings to the focal spot FS of the imager. Shading effects can be reduced and this allows using the available radiation more efficiently.

In the above embodiments, the purpose of the intensity profile modulation was to account for different path lengths through the object to be imaged OB. However, this is not to say that other intensity profile modulations by the proposed grating G0 are excluded herein. They are not. Other intensity profile modulations designed to account for other physical or technical effects in relation to the X-ray imaging process (in particular in CT imaging) are specifically envisaged herein. For instance, in one embodiment the grating G0 is configured to compensate for the Heel effect observed in X-ray tubes. To this end, the duty cycle, absorber bar material and absorber depth etc, are so configured that a decreasing intensity profile is measurable behind the grating along the Z-axis (rotation axis) of the rotational X-ray imaging system. Preferably, the intensity profile decreases monotonically, such as linearly. This can be done by modulating the duty cycle, absorber beam depth, etc as explained above in relation to FIG. 4.

The Heel effect describes the situation where the X-ray beam XB generated by the X-ray source has a non-uniform intensity throughout its cross-section. That is, intensity is lost as a consequence of the way the X-ray beam is generated in the source XR. Loss of intensity is a function of the angle between the emitted rays of the beam XB and the anode surface. Specifically, rays inclined towards the anode already experience intensity loss because of intervening anode material. This effect is less pronounced or even absent for rays that are inclined away from the anode surface (and towards the cathode).

The Heel effect will depend how exactly the XR source is mounted in the imaging system. In other words, the above mentioned embodiment in terms of the z-axis is merely one embodiment. In general therefore it proposed herein to configure the grating G0 and its arrangement in the imaging system so that the Heel effect can be compensated in at least one direction (preferably in all relevant directions).

Figure 5:
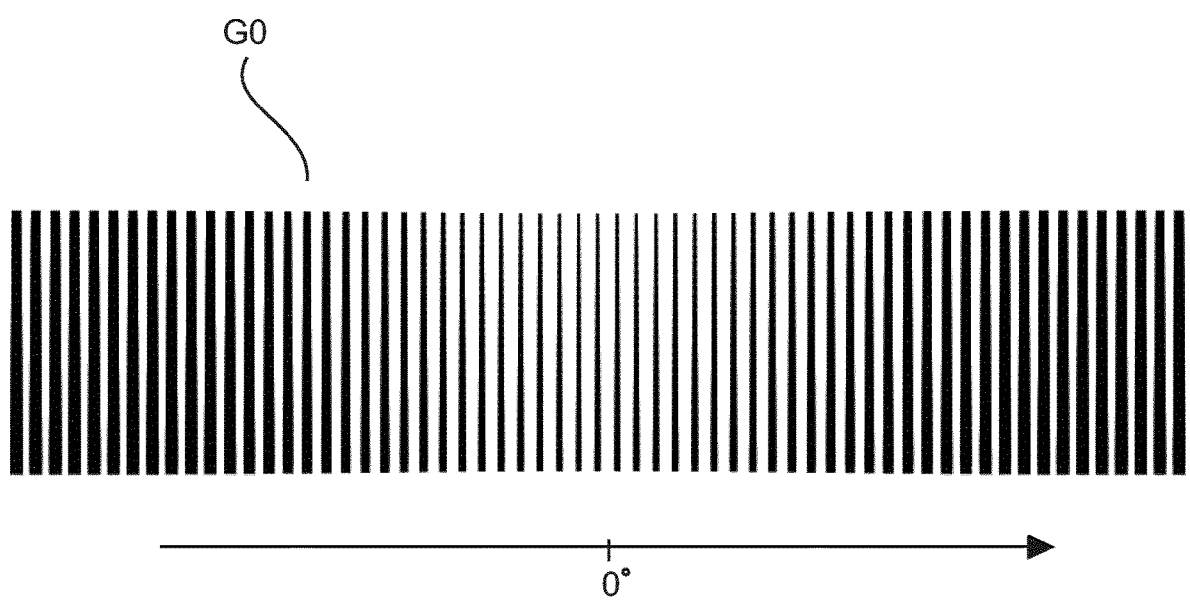
FIG. 5 shows, in plan view, a grating structure according to a further embodiment.

FIG. 5 shows a grating G0 according to one embodiment which is configured to i) improve coherence, ii) to compensate for different object cross-sections (as in FIG. 4) and iii) to compensate for the Heel effect. In the plan view of FIG. 5, the Z-axis runs parallel to the plane of the drawing. In other words, the grating G0 integrates bow-tie functionality (thanks to the, in the view as per FIG. 5, horizontal modulation) and Heel compensator functionality (thanks for the, in the view as per Figure, vertical modulation). Alternatively, the grating may be formed to account only for the Heel effect in which case there is no modulation in horizontal direction.

Other or additional physical or technical effects may also be accounted for by compensation or otherwise, either singly or in combination.

For the sake of completeness it should be mentioned that in order for the grating structure G0 to properly function for interferometric X-ray imaging, specifications other than the duty cycle must be met by grating G0. These specifications are sometimes called "design rules". The duty cycle is in general in the range of 30-50%. Another specification is the "pitch", that is, the spatial period of the absorber elements. This period is typically in the order of 10-100 μm. The aspect ratio describes the ratio between the height/depth of the respective absorber elements and the distance between two neighboring absorber elements (that is, the inter-spaces). Typical aspect ratios are in the order of 30-50 but this is exemplary and depends on the design energy.

The design energy is the energy at which the fringe pattern has maximum visibility, with visibility being an experimentally definable interferometric quantity expressed in term of intensity ratios. Each interferometric set up is in general adjusted to a certain design energy or at least to certain design energy bandwidth around a design energy value. Examples for suitable design energies are for instance 25 keV or 50 keV but these numbers are purely exemplary.

One design rule that involves the grating structure G0 is $d_0/l_0 = p_2/p_0$, where $p_2$ and $p_0$ are the pitches of the analyzer grating $G_2$ and the source grating structure $G_0$ described above. Distance $d_0$ (or Talbot distance) is the distance of a path along the optical axis of the imaging system between grating $G_1$ and grating $G_2$ and distance $l_0$ is the distance between the source grating $G_0$ and phase grating $G_1$.

It should be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a

The invention claimed is:

1. A source grating structure for interferometric X-ray imaging having a non-uniform duty cycle profile behind a surface of the grating structure when exposed to X-ray radiation, wherein the grating is configured to compensate, in a at least one direction, for a Heel effect.

2. The grating structure of claim 1, said duty cycle profile having at least one local maximum away from an edge of said surface.

3. An imaging system, comprising:
   an X-ray source;
   an X-ray sensitive detector;
   an examination region between the X-ray source and the X-ray sensitive detector for receiving an object to be imaged; and
   a source grating structure of claim 1 arranged between the X-ray source and the object when said object resides in the examination region.

4. The imaging system of claim 3, wherein the imaging system is a computed tomography imaging system.

5. A grating structure for interferometric X-ray imaging, comprising a set of absorbing elements arranged in a periodic pattern to form a surface, the set including at least two absorbing elements, one proximal and one distal to an edge of the surface, wherein a material density of the proximal absorbing element is higher than the material density of the distal absorbing element.

6. A grating structure for interferometric X-ray imaging, comprising a set of absorbing elements arranged in a periodic pattern to form a surface, the set including at least two absorbing elements, one proximal and one distal to an edge of the surface, the at least one proximal absorbing element having a greater depth perpendicular to said surface than the depth of the distal absorbing proximal element.

* * * * *